(12) United States Patent
Harrison et al.

(10) Patent No.: US 12,233,174 B2
(45) Date of Patent: Feb. 25, 2025

(54) SYSTEM AND METHOD FOR REDUCING MICROBIAL LOAD USING VIOLET LIGHT

(71) Applicant: KORRUS, INC., Los Angeles, CA (US)

(72) Inventors: Benjamin Harrison, Los Angeles, CA (US); Daniel Ventura, Los Angeles, CA (US); Sina Afshari, Los Angeles, CA (US); Raghuram L. V. Petluri, Los Angeles, CA (US); Paul Kenneth Pickard, Los Angeles, CA (US)

(73) Assignee: KORRUS, INC., Los Angeles, CA (US)

( * ) Notice: Subject to any disclaimer, the term of this patent is extended or adjusted under 35 U.S.C. 154(b) by 753 days.

(21) Appl. No.: 17/229,506

(22) Filed: Apr. 13, 2021

(65) Prior Publication Data
US 2021/0338861 A1    Nov. 4, 2021

Related U.S. Application Data

(60) Provisional application No. 63/009,374, filed on Apr. 13, 2020.

(51) Int. Cl.
*A61L 2/10* (2006.01)
*A61L 2/16* (2006.01)

(52) U.S. Cl.
CPC .................. *A61L 2/10* (2013.01); *A61L 2/16* (2013.01); *A61L 2202/11* (2013.01); *A61L 2202/14* (2013.01); *A61L 2202/25* (2013.01)

(58) Field of Classification Search
CPC .................. A61L 2/10; A61L 2/084
See application file for complete search history.

(56) References Cited

U.S. PATENT DOCUMENTS

| | | | |
|---|---|---|---|
| 9,439,989 B2 * | 9/2016 | Lalicki | A01K 29/00 |
| 11,541,135 B2 * | 1/2023 | Barron | F21K 9/64 |
| 2010/0246169 A1 * | 9/2010 | Anderson | A61N 5/0624 250/492.1 |
| 2017/0014538 A1 * | 1/2017 | Rantala | H01L 33/08 |
| 2019/0022263 A1 * | 1/2019 | Quilici | F21V 21/30 |
| 2019/0298870 A1 * | 10/2019 | Barron | A61L 9/18 |
| 2020/0267814 A1 * | 8/2020 | Song | F21V 23/0435 |

FOREIGN PATENT DOCUMENTS

EP     1557180 A1 *  7/2005  ........... A61L 12/124

* cited by examiner

*Primary Examiner* — Jennifer Wecker
*Assistant Examiner* — Brady C Pilsbury
(74) *Attorney, Agent, or Firm* — FisherBroyles LLP

(57) ABSTRACT

A light source for emitting emitted light to reduce microbial load, said light source, comprising: (a) at least one first light source for emitting first light having a peak wavelength less than 400 nm; and (b) at least one second light source for emitting a second light; wherein said emitted light comprises a combination of said first light and said second light, wherein said emitted light has a spectral power distribution (SPD), wherein said SPD has a first power in said SPD between 350 nm and 800 nm, and a second power in said SPD between 350 nm and 420, wherein said second power is at least 40% of said first power, and wherein said emitted light has a CRI of at least 80.

20 Claims, 2 Drawing Sheets

SYSTEM AND METHOD FOR REDUCING MICROBIAL LOAD USING VIOLET LIGHT

REFERENCE TO RELATED APPLICATIONS

This application is based on U.S. provisional application No. 63/009,374, filed Apr. 13, 2020, which is hereby incorporated by reference in its entirety, including its appendices.

FIELD OF DISCLOSURE

This disclosure relates, generally, to an approach for controlling infection, and, more specifically, to a system and method of adding a relatively short wavelength disinfecting light to a white light source to reduce microbial load, including COVID 19.

BACKGROUND

There is a need to reduce healthcare associated infections (HAI). HAIs effect 2,000,000 people each year in the United States alone. The CDC estimates that 99,000 people die each year from HAI. The direct cost of HAIs is estimated to be between $28 billion and $45 billion per year.

Infection control methods in healthcare settings predominantly involve reducing microbial load at specific times, for example, cleaning a patient's room when the patient is discharged, or spot cleaning high touch areas at regular intervals. But absent continuous disinfection, microbial concentrations quickly return to unacceptable levels. Work on solid state, continuous disinfection through copperization of high touch surfaces has shown that continuous microbial debulking is effective in reducing microbial loads in healthcare settings. This reduction in microbial loads has been shown, in turn, to reduce the rate of nosocomial infections and to improve patient outcomes and reduce costs to providers.

Aside from copperization of high-touch surfaces, healthcare facilities also use disinfecting ultraviolet (UV) light or "ultraviolet germicidal irradiation (UVGI)". Such systems use UV-C radiation to kill or inactivate pathogens by disrupting their DNA or RNA. Applicant recognizes that, while certain rooms can be unoccupied at predictable or scheduled times for UV disinfection (e.g., patient rooms, operating theaters, etc.), the occupancy cannot be controlled/predicted reliably for other areas in healthcare facilities (e.g., waiting rooms, hallways, restrooms etc.), and, thus, high intensity UV disinfection is not an option.

In such cases, continuous disinfection through continuous lighting with nonhazardous disinfecting light is preferred. Moreover, Applicant recognizes that the continuous lighting should be a white light that is on or near the Planckian locus. Therefore, Applicant has identified the need for continuous disinfecting lighting having high-quality whiteness. The present invention fulfills this need among others.

SUMMARY

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Applicant recognizes that continuous disinfection requires higher doses/concentrations disinfecting light to be more effective, but Applicant also understands that increasing this light component can cause an undesirable shift of the light from the Planckian locus. Accordingly, Applicant discloses herein using a shorter wavelength disinfecting light in higher concentrations to provide effective continuous disinfection, and to minimize shift from the Planckian locus. More specifically, Applicant recognizes that a disinfecting light having a shorter wavelength, for example, less than 400 nm, will not be as perceptible to the human eye compared to longer wavelengths (e.g., blue and red), thereby allowing the light system of the present invention to increase the dose concentration of disinfecting light below 400 nm. In other words, the shorter wavelength light can be used in greater proportion to the overall spectrum while having a disproportionally small effect on diminishing the quality of light. For example, Applicant has found that a lighting system with a disinfecting light having a peak wavelength of about 395 nm and a spectral power distribution (SPD) in the range of 380 to 420 nm which is greater than 40% of the overall SPD of the emitted light, maintains good color rendering—e.g., a color rendering index (CRI) of greater than 80.

In one embodiment, Applicant has developed a novel LED technology suitable for continuous disinfection. This LED provides white light for illumination, while delivering safe, germicidal radiation. As these new lights replace existing light sources, anytime the lights are on, the continuous disinfection system of the present invention is active. In one embodiment, the spectrum of the present invention is distinct from traditional LED lighting because a significant fraction of its power (i.e., greater than 40%, 50%, 60% or 65%) is contained in wavelengths shorter than 420 nm. These wavelengths are germicidal via interaction with endogenous photosensitizers. This has been shown to be highly toxic to many microbes of clinical significance. According to well established photobiological safety standards, this technology is not harmful to humans and is exempt from classification for Actinic UV, Near UV, and Blue Light hazards and is therefore safe for use in continuous exposure.

Conversely, traditional illumination LEDs are driven by a 450 nm source and phosphor converted to produce white light. Phosphor conversion increases the wavelength of light, so a system driven by a 450 nm pump tends not to contain meaningful content in the violet and near UV bands. Applicant has designed several LEDs which, in one embodiment, use a 395 nm pump. Furthermore, in one embodiment, Applicant has designed phosphor mixtures to work with this pump and produce white light with a CRI of at least 80 (or at least 85 or 90), meeting (or exceeding) hospital lighting standards. By using this pump, in one embodiment, Applicant's system delivers at least 100%, 150%, 200% or 250% of the germicidal radiation at the same illuminance and color temperature as existing continuous disinfection technologies based on a 405 nm nm pump. This translates to reduced microbial burdens in healthcare settings, thus reducing HAI rates and saving both lives and money.

Beyond the immediate application to healthcare, this technology can be applied in many spaces, including residential care, educational facilities, transportation, retail, and in food preparation.

Specific to the COVID-19 crisis, this technology improves the outcome for patients in intensive care by reducing rates of secondary infections which are found in 50% of non-survivors, as compared to just 1% of survivors. In an ICU operating at capacity, Applicant's technology can cut HAI rates, saving lives, and shortening stays, all without additional work for the staff or compromising safety.

This technology also offers a path to reduced dependence on antibiotics and so may contribute to slowing the development of widespread antibiotic resistance. Early evidence suggests that microbes show minimal ability to adapt to the germicidal effect of violet radiation, so it is expected the development of resistance will take a long time or simply never occur.

In one embodiment, a system is disclosed comprising a light source for reducing microbial load comprising: (a) at least one pump light emitting diode (LED) for emitting pump light having a peak wavelength of about 395 nm; (b) one or more wavelength converting materials for converting a portion of the pump light to converted light such that the light source emits emitted light comprising a combination of the pump light and the converted light, wherein the emitted light has a spectral power distribution (SPD), wherein the SPD has a first power in the SPD between 350 nm and 800 nm, and a second power in the SPD between 350 nm and 420, wherein the second power is at least 40% (or at least 50%, 60% or 65%) of the first power, and wherein the emitted light has a CRI of at least 80 (or at least 85, or 90).

In another embodiment, a method is disclosed comprising exposing a treated surface to emitted light, wherein the emitted light has a spectral power distribution (SPD), wherein the SPD has a first power in the SPD between 350 nm and 800 nm, and a second power in the SPD between 350 nm and 420, wherein the second power is at least 40% (or at least 50%, 60% or 65%) of the first power, and wherein the emitted light has a CRI of at least 80 (or at least 85, or at least 90). In one embodiment, the emitted light is produced by a light source comprising: (a) at least one pump light emitting diode (LED) for emitting pump light having a peak wavelength of about 385 nm; and (b) one or more wavelength converting materials for converting a portion of the pump light to converted light such that the light source emits the emitted light. In one embodiment, the method targets COVID-19 and other clinically relevant pathogens, including *Staphylococcus aureus*, enterococci, and clostridioides *difficile*.

DETAILED DESCRIPTION

Figure 1:
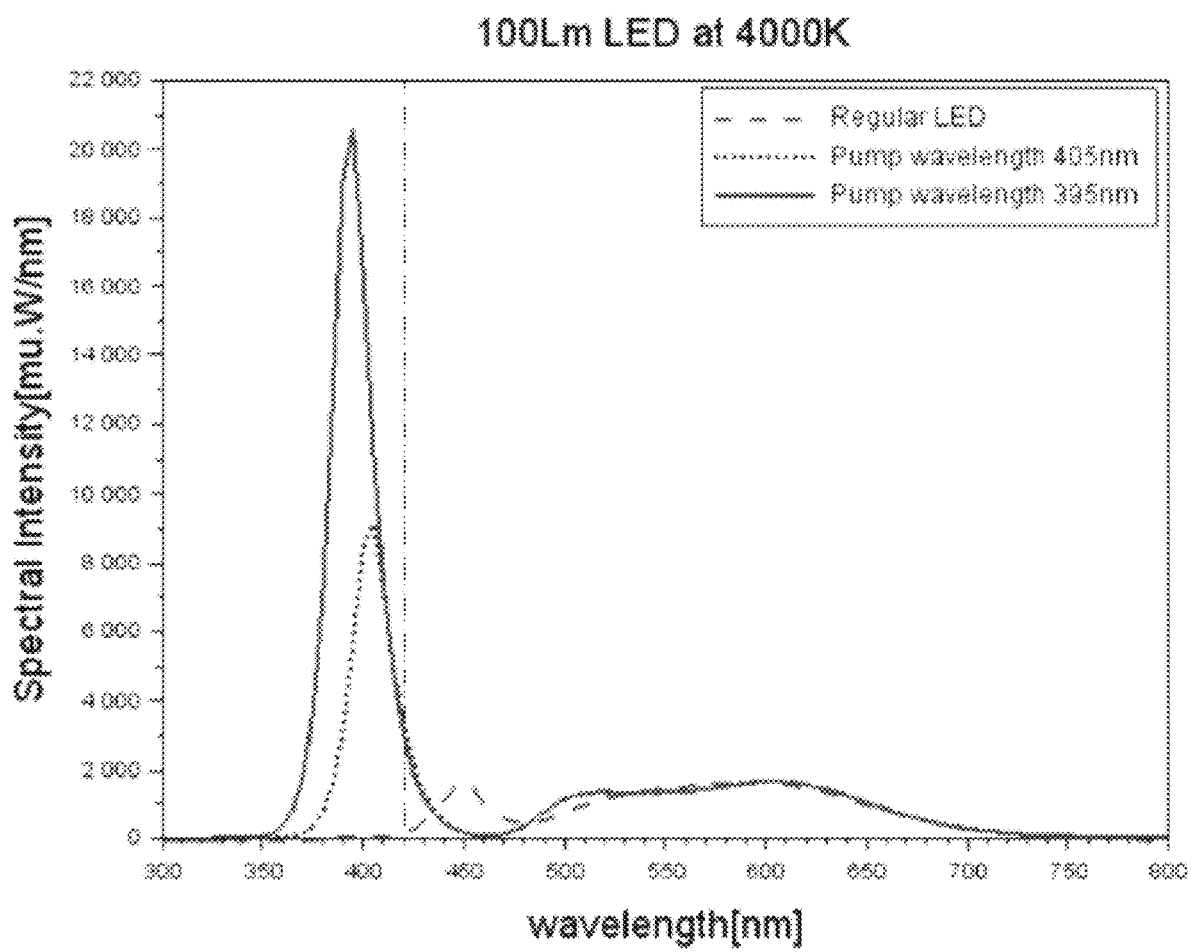
FIG. 1 is a graph comparing different spectra.

In one embodiment, the present invention relates to a system comprising a light source for reducing microbial load comprising: (a) at least one pump light emitting diode (LED) for emitting pump light having a peak wavelength of about 395 nm; (b) one or more wavelength converting materials for converting a portion of the pump light to converted light such that the light source emits emitted light comprising a combination of the pump light and the converted light, wherein the emitted light has a spectral power distribution (SPD), wherein the SPD has a first power in the SPD between 350 nm and 800 nm, and a second power in the SPD between 350 nm and 420, wherein the second power is at least 40% of the first power, and wherein the emitted light has a CRI of at least 80.

In another embodiment, the present invention relates to a method for reducing microbial load on a treated surface. In one embodiment, the method comprises exposing the treated surface to emitted light, wherein the emitted light has a spectral power distribution (SPD), wherein the SPD has a first power in the SPD between 350 nm and 800 nm, and a second power in the SPD between 350 nm and 420, wherein the second power is at least 40% of the first power, and wherein the emitted light has a CRI of at least 80.

Each of these elements as described below in greater detail and with respect to selected alternative embodiments.

Throughout this disclosure, reference is made to the first and second light sources. It should be understood that the first and second light sources refer, respectively, to the light source for emitting the disinfecting light having a peak wavelength of less than 400 nm, and the light source for emitting a second light, which is generally, but not necessarily, white light, on or near the Planckian locus. Although reference is made to two different light sources, the light sources may be discrete or may be combined into a unitary structure.

In one embodiment, the light sources are combined in a single light. For example, in one embodiment, the first light source may be an LED for emitting a first light which also functions as a pump light for pumping wavelength-converting materials, and the second light source comprises wavelength-converting materials for emitting the converted or second light when pumped, such that the emitted light is a combination of the pump light and the converted light. In one embodiment, the first light source comprises a pump LED for emitting a 395 nm pump light which is configured to excite one or more phosphors or quantum dots in the second light source. In one embodiment, the first and second light sources are packaged in a single LED light source. In another embodiment, the second light source is discrete from the first light source. For example, in one embodiment, the wavelength converting materials are at a distance from the LED pump. The wavelength-converting materials may comprise phosphors, quantum dots, or other wavelength converting materials.

Figure 2B:
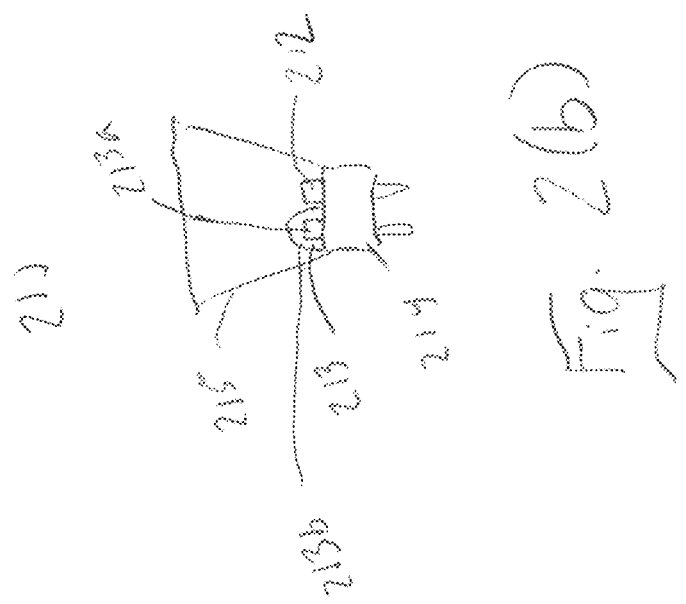
FIG. 2(b) shows a schematic of another embodiment of the light system of the present invention in which the first light source and the second light source are discrete.
Figure 2A:
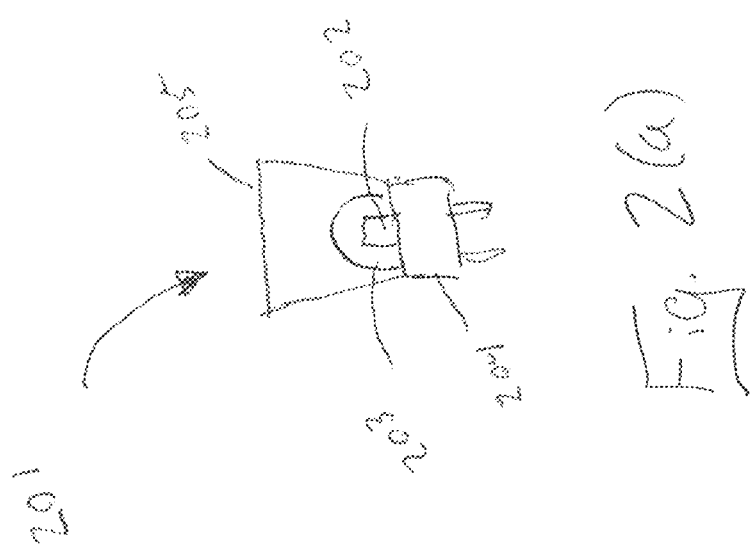
FIG. 2(a) shows a schematic of one embodiment of the light system of the present invention in which the first light source and the second light source are combined.

For example, referring to FIG. 2(a), a schematic of one embodiment of a lamp 201 is shown in which the first light source and the second light source are combined. More specifically, in this embodiment, the first light source 202 is an LED, which is configured to excite the phosphors of the second light source 203. As is known, the light sources are mounted on a base 204 which is configured with an electrical interface for plugging into a known electrical socket. Again, as known, the base comprises an electrical driver for driving the LED. In this particular embodiment, the lamp 201 also comprises a lens or housing 205.

In an alternate embodiment, the first and second light sources are discrete. For example, in such an embodiment, the first light source emits a disinfecting light, while the second light source emits a white light on or near the Planckian locus. As mentioned above, Applicant recognizes that because the disinfecting light is below 400 nm its perception by the human eye is low and has a disproportionately low impact on the quality of the white light of the second light source. Thus, in such an embodiment, the second light source can be optimized for quality of light. In an alternative embodiment, the light emitted from the second light source is slightly above the Planckian Locus, such that, when combined with the first light, the second light is pulled down slightly onto or near the Planckian Locus.

In one embodiment, the second light source comprises one or more wavelength converting materials for converting a portion of the first light to the second light. In one embodiment, the first light source comprises at least one first light emitting diode (LED). In one embodiment, the second light source comprises at least one second LED. In a more particular embodiment, the second light source also comprises one or more wavelength converting materials for converting a portion of light from the second LED to converted light, wherein the second light comprises a combination of the light from the second LED and the converted light. Alternatively, in one embodiment, the at least one second LED comprises a plurality of second LEDs and wherein the second light is a combination of light from the plurality of second LEDs.

For example, referring to FIG. 2(b), a schematic of another embodiment of a lamp 211 is shown in which the first light source and the second light source are discrete. More specifically, in this embodiment, the first light source 212 comprises an LED, and the second light source 213 comprises a second LED 213a for driving phosphors 213b. Like lamp 201, lamp 211 also comprises a base 214 with electrical interface and a lens or housing 215. In this particular embodiment, the base houses two different drivers for driving the first and second light sources 212, 213, independently.

In one embodiment, the first and second light sources are discrete and may be independently driven. In one embodiment, the light sources are independently driven to allow for variability in the relative intensities of the first light and second light. For example, in one embodiment, the first and second light sources are driven independently to increase the amount of disinfecting light when the light system determines that the space being illuminated is unoccupied. In yet another embodiment, if the light system detects that the room is unoccupied, the second light may be turned off completely such that the emitted light comprises only the disinfecting light of the first light source. Still other variations/applications of the light system the present invention in connection with altering the concentration of the first and second light in the emitted light will be obvious to those of skill in the art in light of this disclosure.

In an embodiment in which the first and second light sources are independently driven, it may be desirable to alter the emitted light, not only to optimize microbial suppression, but also to regulate circadian stimulation. For example, in some applications, it may be preferable to reduce the Equivalent Melanopic Lux (EML) of the emitted light—e.g. in the evening prior to a user going asleep. In such an application, one embodiment of the light system of the present invention involves increasing the first light relative to the second light. As is known, light having a wavelength less than 420 nm is low in EML, and, thus, the emitted light with an increased portion of first light would have a reduced EML, thereby reducing circadian stimulation. On the other hand, during the day or at times when the user wants to be more awake/alert, one embodiment of the light system the present invention involves increasing the second light relative to the first light in the emitted light. In this embodiment, the emitted light with have a greater concentration of second light (i.e. white light), which has a high EML compared to the low EML of the first light, and thus, the emitted light will have a higher EML, thereby increasing circadian stimulation. Still other embodiments of the light system the present invention for moderating circadian response will be obvious to those of skill in the art in light of this disclosure.

An important aspect of the present invention is the high concentration of light below 420 nm in the spectrum. In one embodiment, the emitted light comprises a combination of the first light and the second light, wherein the emitted light has a spectral power distribution (SPD), wherein the SPD has a first power in the SPD between 350 nm and 800 nm, and a second power in the SPD between 350 nm and 420, wherein the second power is at least 40% of the first power (or at least 50%, or at least 60% or at least 65%) of the first power, Another important aspect of the invention is the high quality of light it produces while emitting a substantial portion of disinfecting light. In one embodiment, the CRI of the emitted light is no less than 80 (or no less than 85, or no less than 90). As mentioned above, Applicant found that the effect of the first light on the CRI of the emitted light is disproportionately small. In one embodiment, the CRI of the emitted light is no less than 80% (or no less than 85%, or no less than 90%) of the CRI of the second light.

Therefore, Applicant has developed a novel LED technology suitable for continuous disinfection. This LED provides white light for illumination, while delivering safe, germicidal radiation. As these new lights replace existing light sources, anytime the lights are on, the continuous disinfection system of the present invention is active. As seen in FIG. 1, in one embodiment, the spectrum of the present invention shown in solid line is distinct from traditional LED lighting shown in dashed line because a significant fraction of its power—i.e., greater than 65%—is contained in wavelengths shorter than 420 nm (left of the vertical line). These wavelengths are germicidal via interaction with endogenous photosensitizers. This has been shown to be highly toxic to many microbes of clinical significance. According to well established photobiological safety standards, this technology is not harmful to humans and is exempt from classification for Actinic UV, Near UV, and Blue Light hazards and is therefore safe for use in continuous exposure.

Conversely, still referring to FIG. 1, traditional illumination LEDs are driven by a 450 nm source and phosphor converted to produce white light (shown in dashed line). Phosphor conversion increases the wavelength of light, so a system driven by a 450 nm pump tends not to contain meaningful content in the violet and near UV bands. On the other hand, Applicant has designed several LEDs which, in one embodiment, use a 395 nm pump (shown in solid line). Furthermore, in one embodiment, Applicant has designed phosphor mixtures to work with this pump and produce white light with a CRI of at least 80, meeting (or exceeding) hospital lighting standards. By using this pump, in one embodiment, Applicant's system delivers at least 100%, at least 150%, at least 200% or at least 250% of the germicidal radiation at the same illuminance and color temperature as existing continuous disinfection technologies based on a 405 nm pump (shown in dotted line). This translates to reduced microbial burdens in healthcare settings, thus reducing HAI rates and saving both lives and money.

Applicant has found that the light system of the present invention is effective in reducing a variety of microbial load, including COVID-19, *Staphylococcus aureus*, enterococci, and clostridioides *difficile*.

In addition, there is evidence that microbicidal lighting may interact synergistically with commonly used chemical disinfectants, resulting in efficacy exceeding the simple sum of their respective effects.

In one embodiment, the system and method of the present invention focus on high touch elements of the healthcare environment and known microbial reservoirs. High touch areas include bedrails, call buttons, toilet seats, handrails, tray tables and bedclothes. In one embodiment, the treated surface is located in at least one of a kitchen, a hospital room, a nursery, a bathroom, a shower room, a locker room, within a healthcare facility, within an assisted living facility, within a childcare facility, within a food processing facility, or within a school, just to name a few.

EXAMPLES

Table 1 is a compilation of results (e.g., Ra, R9, LER, COI, EML, nUV) from a light source based on one or more pump LEDs (e.g., λ(p1), λ(p2), λ(p3)) in combed with one or more wavelength-converting materials, (e.g., P1, P2, P3). It should be understood that these results are provided for informational purposes only and should not be construed to restrict the scope of the claimed invention.

| | | | | | | | | | | | | |
|---|---|---|---|---|---|---|---|---|---|---|---|---|
| | | | | | 4000K | | | | | | | |
| λ (p1) | λ (p2) | λ (p3) | P1 | P2 | P3 | Ra | R9 | LER | COI | EML | nUV | nUV content for 100 Lm |
| 380 | | | | Luag | M615 | 82.99 | 32.47 | 46.93 | 5.36 | 0.64 | 0.86 | |
| 395 | | | | Yag | M615 | 66.05 | −22.19 | 112.14 | 9.58 | 0.49 | 0.69 | |
| 395 | | | | Luag | M615 | 83.03 | 32.86 | 118.42 | 5.74 | 0.66 | 0.64 | 542724.160 |
| 380 | | | pcB | Luag | M615 | 93.96 | 52.8 | 112.46 | 4.28 | 0.76 | 0.64 | |
| 395 | 405 (4:1) | | | Yag | M615 | 65.80 | −23.4 | 137.42 | 9.5 | 0.49 | 0.63 | |
| 395 | 405 (2:1) | | | Luag | M615 | 83.32 | 33.14 | 146.3 | 5.65 | 0.65 | 0.55 | |
| 395 | RB3 (21:1) | | | Luag | M615 | 85.54 | 35.61 | 149.26 | 5.45 | 0.67 | 0.54 | |
| 395 + 405 | (1:1) | | | Luag | M615 | 83.35 | 32.80 | 161.97 | 5.63 | 0.65 | 0.51 | |
| 380 | 430 (11.1) | | | Luag | M615 | 85.74 | 36.75 | 163.38 | 5.36 | 0.67 | 0.48 | |
| 395 | 430 (6:1) | | | Yag | M615 | 67.26 | −19.12 | 182.38 | 9.1 | 0.50 | 0.47 | |
| 395 | 430 (11:1) | | | Luag | M615 | 86.71 | 36.73 | 169.47 | 5.43 | 0.63 | 0.46 | |
| 405 | | | | Luag | M615 | 83.78 | 33.19 | 189.87 | 5.34 | 0.65 | 0.42 | 21947.900 |
| 395 | RB3 (5:1) | | | Yag | M615 | 71.64 | 1.05 | 197.32 | 7.53 | 0.54 | 0.41 | |
| 405 | 430 (42:1) | | | Luag | M615 | 84.10 | 34.73 | 192.9 | 5.55 | 0.65 | 0.40 | |
| 395 | RB3 (5:1) | | | Yag | M630 | 71.61 | 0.21 | 203.21 | 7.34 | 0.53 | 0.40 | |
| 405 | RB3 (32:1) | | | Luag | M615 | 84.38 | 34.66 | 196.75 | 5.49 | 0.66 | 0.39 | |
| 395 | RB4 (5:1) | | | Yag | M615 | 71.64 | −11.95 | 210.63 | 8.44 | 0.55 | 0.39 | |
| 395 | RB4 (5:1) | | | Yag | M630 | 74.06 | 7.09 | 206.46 | 7.07 | 0.56 | 0.38 | |
| 395 | RB3 (4:1) | | | Luag | M615 | 70.23 | −14.11 | 221.20 | 8.60 | 0.53 | 0.36 | |
| 395 | RB3 (5:1) | | | Yag | M615 | 88.08 | 39.50 | 206.33 | 5.10 | 0.68 | 0.35 | |
| 395 | RB4 (5:1) | | | Luag | M615 | 89.70 | 41.78 | 207.57 | 4.97 | 0.70 | 0.34 | |
| 395 | RB3 (3:1) | AIGaN615 | | Yag | | 74.83 | 18.87 | 239.43 | 6.16 | 0.54 | 0.31 | |
| 380 | RB3 (5:1) | | | Luag | M615 | 89.17 | 39.74 | 228.88 | 4.73 | 0.69 | 0.27 | |
| 395 | RB3 (2:1) | AIGaN615 | | Luag | | 82.37 | 54.37 | 261.06 | 3.40 | .75 | .21 | |

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A light source for emitting emitted light to reduce microbial load, said light source, comprising:
    at least one first light source for emitting a first light having a peak wavelength less than 400 nm; and
    at least one second light source for emitting a second light, said second light being white light having a second light Color Rendering Index (CRI);
    wherein said emitted light comprises a combination of said first light and said second light, wherein said emitted light has a spectral power distribution (SPD), wherein said SPD has a first power in said SPD between 350 nm and 800 nm, and a second power in said SPD between 350 nm and 420, wherein said second power is at least 40% of said first power, and wherein said emitted light has an emitted light CRI of at least 80; and
    wherein said emitted light CRI is less than said second light CRI but no less than 80% of said second light CRI.

2. The light source of claim 1, wherein said peak wavelength is greater than 380 nm.

3. The light source of claim 2, wherein said peak wavelength is about 395 nm.

4. The light source of claim 1, wherein said second light source comprises one or more wavelength converting materials for converting a portion of said first light to said second light.

5. The light source of claim 1, wherein said first light source comprises at least one first light emitting diode (LED).

6. The light source of claim 5, wherein said second light source comprises at least one second LED.

7. The light source of claim 6, wherein said second light source also comprises one or more wavelength converting materials for converting a portion of light from said second LED to converted light, wherein said second light comprises a combination of said light from said second LED and said converted light.

8. The light source of claim 6, wherein said at least one second LED comprises a plurality of second LEDs and wherein said second light is a combination of light from said plurality of second LEDs.

9. The light source of claim 6, wherein said first and second light sources are independently driven.

10. The light source of claim 9, wherein the relative intensities of said first light and second light are controllable.

11. The light source of claim 1, wherein the CRI of said emitted light is no less than 90% of the CRI of said second light.

12. The light source of claim 1, wherein said second power is at least 60% of said first power.

13. The light source of claim 1, wherein said second power is at least 65% of said first power.

14. A method for reducing microbial load on a treated surface comprising:
 exposing said treated surface to emitted light, wherein said emitted light comprises a first light having peak wavelength less than 400 nm and a second light, said second light being a white light having a second light CRI, wherein said emitted light has a spectral power distribution (SPD), wherein said SPD has a first power in said SPD between 350 nm and 800 nm, and a second power in said SPD between 350 nm and 420, wherein said second power is at least 40% of said first power, and wherein said emitted light has an emitted light CRI of at least 80 which is less than a second light CRI but is no less than 80% of said second light CRI.

15. The method of claim 14, wherein said emitted light is produced by a light source comprising:
 at least one first light source for emitting first light having a peak wavelength less than 400 nm; and
 at least one second light source for emitting a second light;
 wherein said emitted light comprises a combination of said first light and said second light.

16. The method of claim 15, wherein said first and second light sources are independently driven to control the relative power of said first light and second light in said emitted light.

17. The method of claim 15, wherein light system has a high equivalent melanopic lux (EML) mode and a low EML mode, wherein in said high EML mode, the power of said first light is relatively high to the power of said second light, and, in said low EML mode, the power of said first light is relatively low compared to the power of said second light.

18. The method of claim 14, wherein said second power is at least 60% of said first power.

19. The method of claim 14, wherein said treated surface is located in at least one of a kitchen, a hospital room, a nursery, a bathroom, a shower room, a locker room, within a healthcare facility, within an assisted living facility, within a childcare facility, within a food processing facility, within a school.

20. The method of claim 14, wherein said emitted light interacts with chemical disinfectants, resulting in efficacy exceeding the simple sum of their respective effects.

* * * * *